United States Patent [19]

Bieringer

[11] Patent Number: 4,500,203

[45] Date of Patent: Feb. 19, 1985

[54] METHOD AND APPARATUS FOR INSPECTING ARTICLES

[75] Inventor: Robert J. Bieringer, Toledo, Ohio

[73] Assignee: Owens-Illinois, Inc., Toledo, Ohio

[21] Appl. No.: 429,777

[22] Filed: Sep. 30, 1982

[51] Int. Cl.³ ............................................. G01N 21/90
[52] U.S. Cl. .................... 356/240; 209/525; 250/223 B; 356/394
[58] Field of Search .............. 356/240, 376, 384, 390, 356/394; 250/222.1, 223 R, 223 B; 209/524, 525; 358/101, 106, 107

[56] References Cited

U.S. PATENT DOCUMENTS

| | | | |
|---|---|---|---|
| 2,798,605 | 7/1957 | Richards | 358/106 X |
| 3,549,890 | 12/1970 | Keller | 250/223 B X |
| 3,787,700 | 1/1974 | Chasson | 250/223 X |
| 3,932,042 | 1/1976 | Faani et al. | 356/240 |
| 4,064,534 | 12/1977 | Chen et al. | 358/101 X |
| 4,280,624 | 7/1981 | Ford | 356/240 X |

Primary Examiner—Davis L. Willis
Assistant Examiner—Matthew W. Koren
Attorney, Agent, or Firm—Gerald T. Welch; Myron E. Click

[57] ABSTRACT

Apparatus for inspecting glass containers for irregularities in shape, wherein the containers are moved, in line, on a conveyor past a viewing station where there are three strobed light sources positioned at one side of the conveyor. One light is at 90° with respect to the conveyor while the other two are at 45° angles on either side thereof. Between the lights and the container being inspected are positioned Fresnel lenses; solid state discrete array cameras are positioned behind Fresnel lenses mounted on the opposite side of the conveyor with their viewing axes directed toward the light sources.

Each backlighted container is viewed by the three cameras simultaneously and provides a profile scan of the container at a plurality of planar elevations. These scans are processed and compared electronically with input data fed to a central processing unit. A second embodiment uses an anamorphic lens on each cameras which provides a convenient system for viewing tall bottles while also utilizing the full width of the viewing area by reducing the height to diameter ratio of the bottle image.

23 Claims, 7 Drawing Figures

METHOD AND APPARATUS FOR INSPECTING ARTICLES

BACKGROUND OF THE INVENTION

1. Field of the Invention

This invention relates to inspecting articles and particularly to measuring the shape or profile of hollow containers such as glass containers having a generally cylindrical shape, with normally oval cross-section.

In the manufacture, filling, handling and dispensing of hollow containers it is necessary that the containers be of uniform size and shape in order that high-speed filling and handling machinery can be employed. Such uniformity of size and shape is also required because any variations in size and shape will be readily apparent after filling since the level of the contents will vary when the contents are filled with a predetermined volume. It is therefore important to reject containers during manufacture which vary from a predetermined standard size and shape in the manufacture of economical high quality products. Heretofore, this evaluation has been primarily by manual and off-line methods which of course are subject to human error and provide only a sampling of the normal production.

It is an object of this invention to provide a method and apparatus for automatically measuring the shape or profile of an article such as a glass container, preferably on the production line, so that the container can be rejected as unsatisfactory for packaging purposes.

It is a further object of this invention to provide such a method and apparatus which utilizes light rays so that there is no physical contact of apparatus with the glass container.

It is a further object of this invention to provide novel means for measuring the precise shape or profile of an article such as a glass container to insure uniformity of manufacture.

SUMMARY OF THE INVENTION

Basically the invention comprises horizontally scanning successive transverse areas of the projected two-dimensional image of an upright container without rotation about its longitudinal axis. The container is viewed from at least three different positions and at least three images in profile are formed on similar photosensors which permit determination of the maximum and minimum diameters of the container at a number of given elevations. The fluctuation or changes in light energy at the viewed vertical edges of the container are detected by and produce an electrical signal which is amplified and employed to rapidly calculate such maximum and minimum diameters and deviations from established minimum and maximum dimensions independently of orientation. The container can be illuminated in various ways such as by employing stroboscopic lamps. A plurality of similar photosensors can be employed which are able to detect an image of the profile of the back-lighted container.

Preferably three lamps are located along one side of the conveyor which is transporting the container and three similar photosensors are located along the other side of the conveyor, each lamp and sensor pair being in juxtaposition with the container in line-of-sight therebetween. Each lamp and sensor pair is able to measure the extremities of the container at one elevation, all pairs similarly measuring the container at the same elevations to provide at least three individual measurements for each elevation. Electronic calculation can be used to determine the maximum and minimum diameters of the container at each elevation independently of orientation or position of the container during measurement. Such calculation permits determination of whether such values exceed established dimensions to facilitate rejection of containers failing to meet minimum or maximum dimensions.

DESCRIPTION OF THE PREFERRED EMBODIMENT

This invention provides non-contacting measurement of the outside diameter or profile preferably at several elevations of a freestanding article either stationarily retained or moving on a conveyor. Preferably, three two-dimensional profiles of the article are obtained using strobed illumination; in addition a subset of two orthogonal views can be employed to also obtain the degree of tipping or inclination of the article from the vertical.

The subject invention relates to both method and apparatus using either continuous or strobed back-lighted illumination to obtain three two-dimensional profiles of a moving article obviating the need for an ultra-stable conveyor or transport system and providing data and logic for determination of both maximum and minimum outside diameter. The invention may also be used for measuring articles having cross-sections exhibiting elliptical ovality or deviation from a circle. The several measurements are most desirably made at a number of transverse cross-sectional elevations and may also be employed to measure the degree of tipping or inclination of the article from vertical such as represented by a "leaner" or "rocker" bottom container. Prior art techniques either use beam interruption or do not provide sufficient information to determine both maximum and minimum diameters especially for articles exhibiting ovality.

Figure 1:
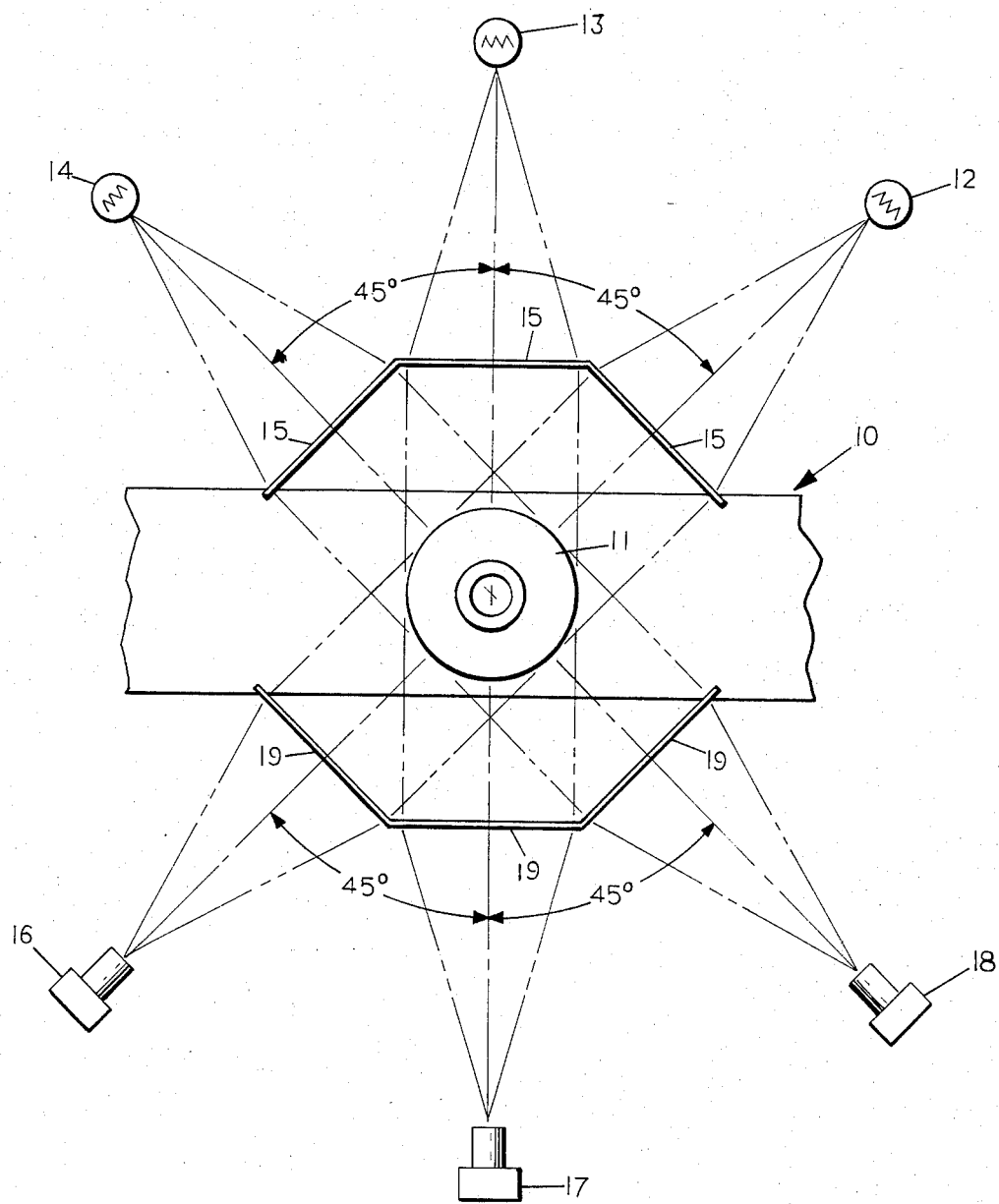
FIG. 1 is a schematic plan view of the apparatus for practicing the invention.

As shown in FIG. 1, the apparatus for practicing the invention is preferably mounted adjacent to a conveyor 10 for transporting bottles 11 serially in upright relation. A series of three similar light sources 12, 13 and 14 are located along one side of the conveyor, preferably at an angle of 45°, 90° and 135° with respect to the direction of movement of the conveyor. A Fresnel lens 15 is mounted between each light source and the bottle 11 as shown in FIG. 1. Such lens cause roughly collimated light to pass through the bottle and to darken and precisely outline its profile when the lamp is illuminated. On the opposite side of conveyor 10 is located a series of three light-receiving cameras 16, 17 and 18 adapted to receive light from each of the opposed light sources 12, 13 and 14. A series of three similar Fresnel lens 19 is located to receive the light passing through the bottle and direct it into the proper camera lens. Thus, the light sources can be strobed to operate simultaneously or in sequence when the bottle is in proper position on the conveyor during its continuous rapid movement past the inspection apparatus.

Figure 2:
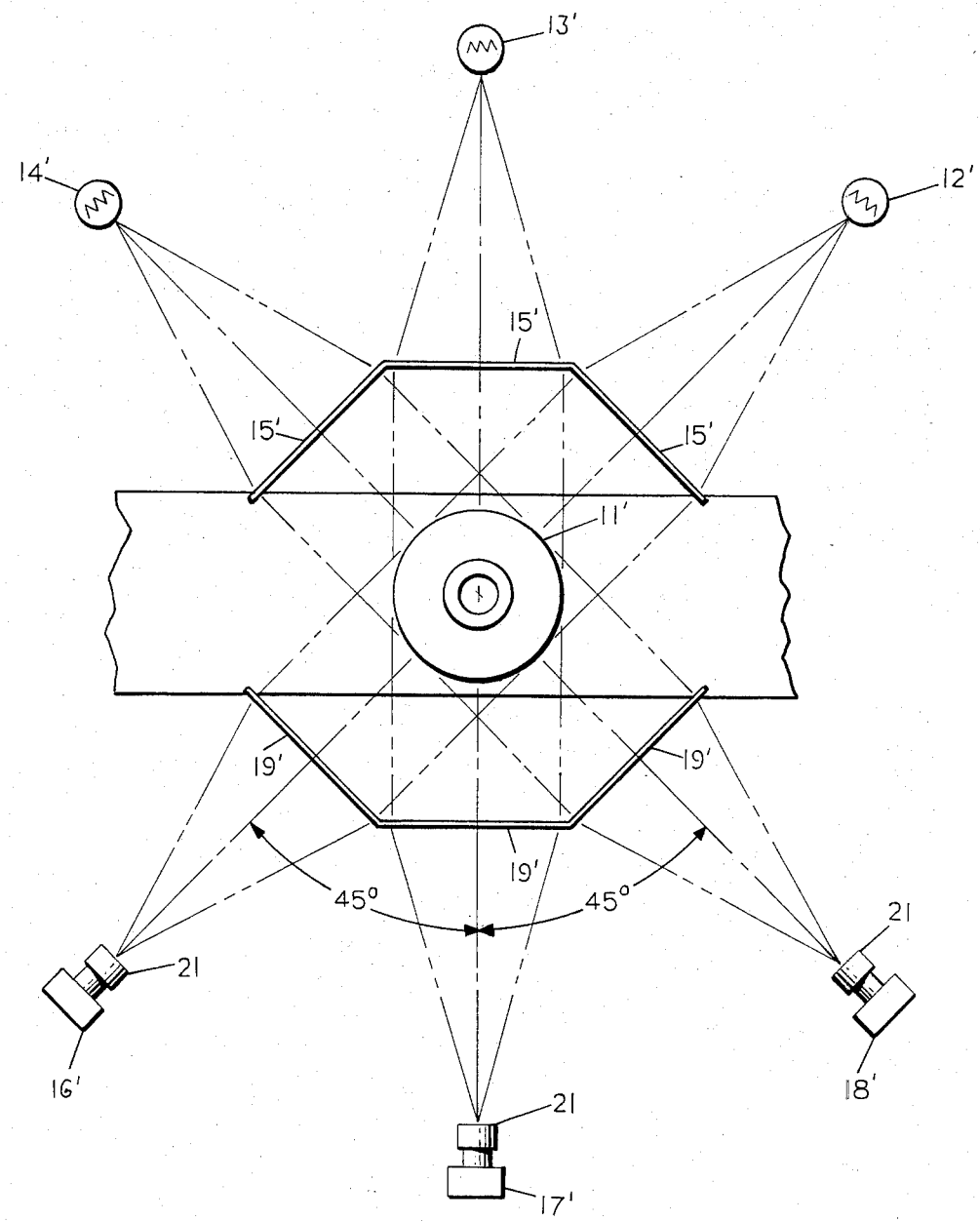
FIG. 2 is a schematic plan view of a modified apparatus for practicing the invention employing an anamorphic lens.
Figure 3:
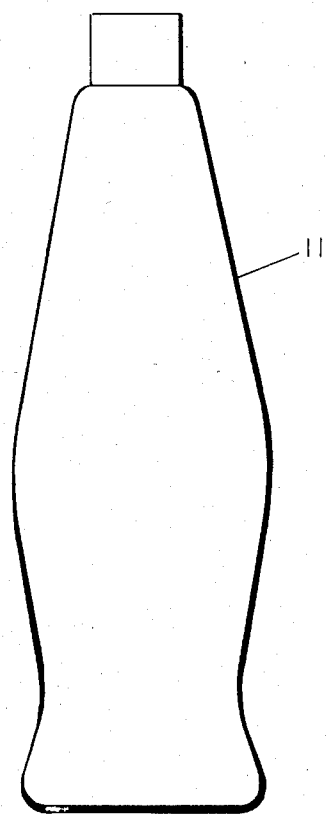
FIG. 3 is a side elevational view of a circular glass bottle to be inspected in accordance with the present invention.
Figure 6:
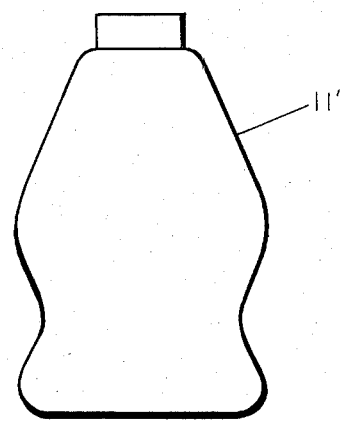
FIG. 6 is a view of the circular glass bottle of FIG. 3 as viewed when employing the anamorphic lens of FIG. 2.

In the case of large bottles such as wine bottles having a considerable height to diameter ratio, an anamorphic lens 21 is mounted on the camera lens of each of the three cameras 16', 17', and 18' of FIG. 2. The apparatus as shown in FIG. 2 is basically the same as shown in FIG. 1 except for the addition of such special lens. The anamorphic lens is able to reduce the height to diameter ratio of the bottle by about 2 to 1, for example, in order to provide greater resolution of the image especially in its horizontal dimension. FIG. 3 illustrates the image of the profile of a typical circular bottle on the camera lens of FIG. 1, while FIG. 6 illustrates the image of the profile of the same bottle 11 using the anamorphic lens 21 of FIG. 2.

Figure 5:
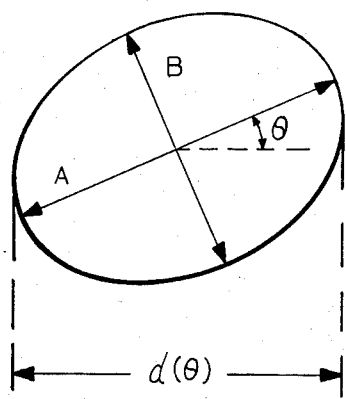
FIG. 5 is a top plan view similar to FIG. 4 illustrating a glass bottle which has an oval cross-sectional shape.
Figure 4:
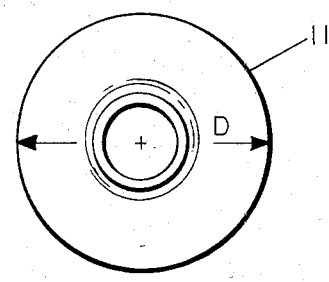
FIG. 4 is a top plan view of the glass bottle of FIG. 3.

The apparatus illustrated in both FIGS. 1 and 2 may be used to measure the diameters of both truly circular bottles 11 as shown in FIG. 4 as well as oval bottles 11 as shown in FIG. 5.

The method is described hereinafter with reference to one of several possible applications. A preferred use of the technique involves on-line gauging of glass bottles during their conveyance, however, it is recognized that gauging of opaque articles is simpler and also within the purview of this invention. FIG. 1 shows a plan view of a typical glass bottle conveyor and one transported bottle along with the preferred viewing aspects for a three camera system. The bottle is back-lighted by strobed illumination in order to eliminate motion blur in its recorded images using a separate lighting source for each viewing aspect. The illumination is roughly collimated in order to provide a two-dimensional profile representative of the extremity of the bottle contour for transparent articles such as transparent glass bottles. Near-collimated illumination also produces, due to refraction, easily sensed dark bottle edges in the two-dimensional profile.

The bottles may be lighted by bulb-type, pulsed Xenon flashtubes such as manufactured and sold by E. G. and G, Electro-Optics Division, Salem, Mass. Such devices are capable of producing short flash duration, high radiance, precise arc-discharge pattern, high pulse rate, and long life in applications requiring light beam sources. As stated, a Fresnel lens is located between each light source and the article to be inspected to provide essentially collimated light to back-light the article in profile.

A schematic representation of the profile of the glass bottle as seen by one of the two-dimensional cameras is shown in FIG. 3. Each of the cameras contains a two-dimensional array of photosensors or pixels so that by counting pixels between edges, one can determine distances in object space for known or calibrated magnification. Once the separation between bottle edges is found at a given elevation their midpoint is taken as the location of the center line at that elevation, e.g. at the base and the lip. The separation at these points is the projection of bottle "lean" or inclination onto the view of the camera, and designated, for example as $R_x$. This is true irrespective of the azimuthal orientation of the container. If one made the same measurements for an orthogonal viewing aspect to obtain a value $R_y$ then the magnitude of the lean R can be obtained from $R^2 = R_x^2 + R_y^2$. In the configuration of FIG. 1 the two orthogonal or perpendicular views can be obtained using cameras 16 and 18.

The three cameras are all similar and preferably consist of one of the Fairchild CCD 2000 series area cameras relying on the precision and reliability of the high resolution solid state charge coupled device image detectors useful in a wide variety of video applications. Such cameras are employed in non-contact optical measurement, optical data acquisition, and television image detection applications, and are preferred in this invention primarily due to their lack of geometric distortion of the image and high resolution.

The actual camera lenses are commercially available. Photographic lenses having an 18 mm format, and depending upon object size, focal lengths of 50, 75 or 100 mm are desirable. Such lenses are available from a number of companies, such as Nikon and Fujinon Companies of Japan.

For a container of circular cross-section its exterior diameter at a given elevation is unique and normally can be determined from a single transverse measurement. This is true where the container is truly a right-circular cylindrical shape having a uniform diameter D at its body portion. However, this is not true for many containers which exhibit ovality such as shown schematically for a single cross-section in FIG. 5. The single measurement of separation of the extremities of the container is not sufficient to obtain major and minor diameters A and B, since A, B and $\theta$ are unknown. Three measurements are required under the assumption of eliptical ovality. Measurements of $d(\theta)$, $d(\theta+45°)$ and $d(\theta-45°)$ yield A and B uniquely for arbitrary $\theta$ while the choices of + and −45° angles result in considerable mathematical simplification. The required mathematical logic and derivation are given hereinbelow, and apply independently to each of a multitude of elevations at which major and minor diameters are to be determined.

Referring to FIG. 5, the dimension $d(\theta)$ is given by $$d(\theta) = \sqrt{A^2 \cos^2 \theta + B^2 \sin^2 \theta}.$$

The three unknowns (A, B, $\theta$) can be determined from the results of three independent measurements of d (such as $d(\theta)$, $d(\theta+\Phi_1)$ and $d(\theta+\Phi_2)$) by solving three simultaneous equations. In general, any values of $\Phi_1$ and $\Phi_2$ can be chosen; however, considerable mathematical simplicity results if we choose $\Phi_1 = -\Phi_2 = 45°$. To further simplify the notation, define the following parameters:

$d_o \equiv d(\theta)$,
$d_+ \equiv d(\theta+45°)$,
$d_- \equiv d(\theta-45°)$ and
$S \equiv \sin \theta$,
$C \equiv \cos \theta$.

Making use of known trigonometric identities, one obtains $$d_o^2 = A^2 C^2 + B^2 S^2$$

$$d_+^2 = \tfrac{1}{2}[A^2(S-C)^2 + B^2(S+C)^2]$$

$$d_-^2 = \tfrac{1}{2}[A^2(S+C)^2 + B^2(S-C)^2]$$

and $$d_-^2 + d_-^2 = A^2 + B^2 \equiv \gamma_+$$

$$d_-^2 - d_-^2 = -2SC(A^2 - B^2) \equiv \gamma_-$$

$$d_o^2 \equiv \gamma_o$$

Thus, $\gamma_+$, $\gamma_-$ and $\gamma_o$ are "measured" quantities and the desired dimensions A and B can be determined by algebraic elimination of dependences upon $\theta$:

$$B^2 = \gamma_+ - A^2$$

$$\gamma_- = 2S\sqrt{1-S^2}(\gamma_+ - 2A^2)$$

$$\gamma_o = A^2 + S^2(\gamma_+ - 2A^2)$$

Algebraic manipulation then leads to the quadratic equation:

$$(A^2)^2 - \gamma_+ A^2 + \gamma_o(\gamma_+ - \gamma_o) - (\gamma_-/2)^2 = 0$$

from which $$A^2 = \gamma_+/2 \pm \tfrac{1}{2}\sqrt{\gamma_-^2 + (2\gamma_o - \gamma_+)^2}$$

The sign can be determined via numerical calculation and shown to be positive. Similar results obtain for $B^2$. Expressions for the unknowns A and B can then be summarized, in compact form, as:

$$A = \sqrt{\tfrac{1}{2}(\gamma_+ + \delta)}, \; B = \sqrt{\tfrac{1}{2}(\gamma_+ - \delta)}$$

with $$\delta = \sqrt{\gamma_-^2 + (2\gamma_o - \gamma_+)^2}$$

and $$\gamma_+ = d_+^2 + d_-^2, \; \gamma_- = d_+^2 - d_-^2,$$

$$\gamma_o = d_o^2.$$

The precision of measurement of $d(\theta)$ is dependent upon camera resolution. For a solid-state discrete array camera which is used to provide geometric linearity, the basic resolution is determined by the number of pixels n contained in the distance $d(\theta)$, i.e. $d(\theta)/n$. Since dimensions to be measured are generally horizontal, it is advantageous to essentially fill the horizontal extent of the camera field with the imaged horizontal extent of the container. For tall thin bottles such as wine bottles, this is not usually possible if one wishes to retain the image of the entire bottle including its vertical extent. However, if one images the container with an anamorphic lens system (one which exhibits different magnification in the horizontal and vertical planes), one can obtain in the image the transformation illustrated in FIG. 6. Anamorphic imaging can be effected by using either a combination of spherical plus cylindrical lens or a pair of crossed cylindrical lenses of different power. One such commercial anamorphic attachment lens can be purchased from D.O. Industries, Kawa Optical Division, East Rochester, N.Y., Model No. 16H being especially useful in this invention. The lens is able to effect a 2 to 1 change in its width to height ratio, the container being reduced to ½ its normal height while shown in its full horizontal or width dimension.

ELECTRONIC IMPLEMENTATION

The measurements described above are implemented electronically using a microprocessor-based system. In view of the general approach being somewhat familiar to those skilled in the art, the requisite components are described herein referring to the schematic block diagram layout of FIG. 7. To obtain high resolution and geometric linearity, the cameras employed in the preferred embodiment are OEM versions of the Fairchild CCD 2000; a solid-state array of 488×380 sensors or pixels which are scanned in television compatible format. To improve horizontal resolution the cameras are each rotated 90° from their normal orientation to align the 488 pixel aspect with the horizontal direction. The central processing unit (CPU) is preferably the Intel 8086 microprocessor with the 8087 arithmetic co-processor added to increase computational speed.

Figure 7:
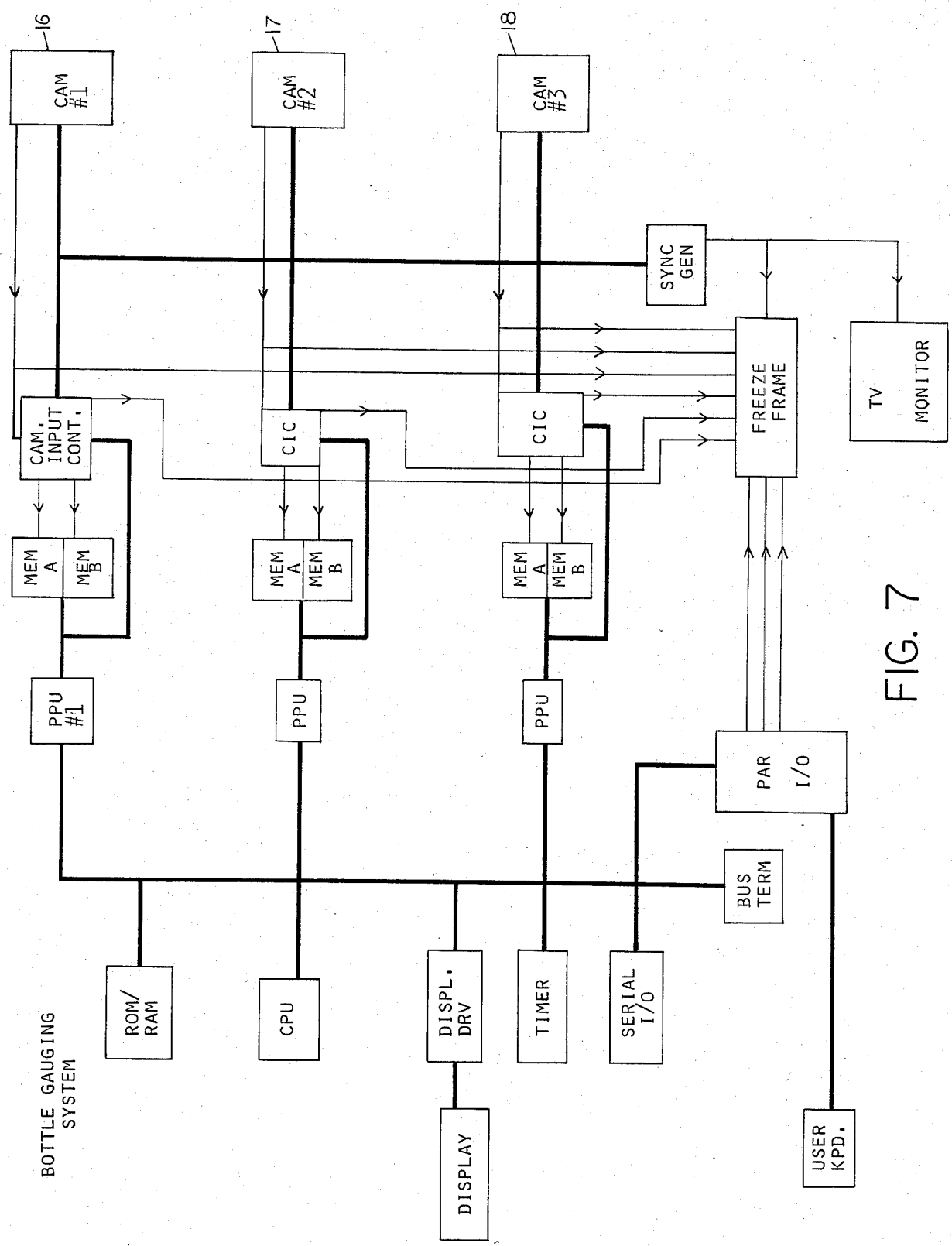
FIG. 7 is a schematic block diagram of the electronic apparatus for practicing the invention.

As shown in FIG. 7, all interconnects to the right of the picture-processing units (PPUs) are made by means of multilead ribbon cable and those to the left are made by means of the common motherboard data bus. The bus is also conditioned against ringing, noise, etc., by means of the bus termination (Bus. Term.).

Each camera has associated with it a camera input controller (CIC), a flip-flop memory (MEM A/B), and a picture-processing unit (PPU). The CIC determines wherein in the camera scan the measurement data are taken and in which area of MEM A/B these data are loaded. The flip-flop memory allows the PPU to process one measurement while the CIC is acquiring data on the next object to be measured. The PPU analyzes the data in MEM A/B to determine the "measured" quantity d for each height. These quantities are passed to the CPU for further analysis.

The CPU completes the procedure by determining the min/max diameters from the d quantities obtained from the three PPUs using calibration parameters stored in random access memory (RAM). The min/max values are compared to user-defined limits also stored in RAM. If the limits are exceeded, a reject signal is activated. The CPU control and analysis programming are stored in read-only memory (ROM).

Operator input of measurement tolerances and positions is accomplished using the parallel input/output (PAR I/O). The reject signal is also controlled through the PAR I/O.

An image buffer memory (Freeze Frame) stores a measurement image and displays it and the appropriate cursor positions on a TV monitor. Results are output to a display via the display driver (Displ. Drv.). Also shown are an optional programmable timer and additional serial I/O.

Various modifications of the present invention can be resorted to within the spirit and scope of the appended claims.

I claim:

1. The method of inspecting the shape of a generally cylindrical or oval article which comprises the steps of illuminating the said article with a series of three lamps located at three different angles along one side of said article, scanning the profile of the illuminated article with a series of three similar photosensors located in fixed juxtaposition at three different complemental angles along the other side of said article during operation of the juxtaposed lamps, measuring the extremities of each of the three profiles of said article at the same planar elevation to permit calculation of the major and minor axes of said article independently of orientation, and rejecting the said article as defective when the deviation of the major and minor axes exceeds established maximum or minimum dimensions.

2. The method in accordance with claim 1, including the step of converting the scanned light rays to electrical impulses by a rectangular planar matrix of pixels in each photosensor to image the complete article in profile to facilitate electronic calculation of deviation of the article major and minor axes.

3. The method in accordance with claim 1, including the step of measuring the extremities of each of the three profiles of said article at two or more planar elevations.

4. The method in accordance with claim 1, including the step of locating a lens system intermediate each of the said three lamps and said article to illuminate said article in back-lighted profile with essentially collimated light.

5. The method in accordance with claim 1, including the step of locating an anamorphic lens system intermediate said article and said series of three similar photosensors to increase the width-to-height viewing ratio of said article.

6. The method in accordance with claim 1, wherein the said article comprises a hollow glass container having a cylindrical shape.

7. The method in accordance with claim 1, including the step of comparing deviation of the article profiles to detect ovality in a right-cylindrical article.

8. The method in accordance with claim 1, including the step of comparing deviation of the article profiles to detect non-uniform ovality in an oval article.

9. The method in accordance with claim 1, including the step of comparing deviation of the article profiles to detect resting inclination of said article with respect to the vertical.

10. The method in accordance with claim 1, including the step of making the measurements during continuous movement of said article past the said series of lamps and photosensors during the scanning of the article profiles.

11. The method in accordance with claim 1, including the step of measuring said article at a plurality of planar elevations during each profile scan of the said article.

12. The method in accordance with claim 1, wherein the said series of three lamps and said series of three similar photosensors are located at 45°, 90° and 135° to the said article, each pair of lamp and photosensor being juxtaposed from each other with said article disposed therebetween in line-of-sight location.

13. The method of inspecting the shape of a generally cylindrical or oval hollow container which comprises the steps of continuously moving the said container in a lineal direction, illuminating the said container with a series of three stroboscopic lamps located at three different angles along one side of the container conveyor, energizing the said lamps when said container is intermediate the said three lamps, scanning the two-dimensional profile of said container at the same elevation with a series of three similar photosensors each located in juxtaposition to one of said lamps at three different complemental angles along the other side of said container during respective operation of the juxtaposed lamps, obtaining at least one measurement at the same elevation from each of the three profiles which permit calculation of the major and minor axes of said container independently of orientation, and rejecting the said container as defective when the deviation of the major and minor axes exceeds established maximum or minimum dimensions.

14. The method in accordance with claim 13, including the step of positioning a lens system intermediate said series of stroboscopic lamps and said container to illuminate said container in back-lighted profile with essentially collimated light.

15. The method in accordance with claim 13, including the step of positioning an anamorphic lens system intermediate said container and said series of three photosensors to increase the width-to-height viewing ratio of said container.

16. The method in accordance with claim 13, including the step of obtaining measurements of maximum and minimum diameter and angular orientation at least at three different planar elevations of said container to calculate the extent of ovality and the degree of resting inclination of said container.

17. The method in accordance with claim 13, including the step of continuously transporting said container in upright relation past the said series of stroboscopic lamps and photosensors, and measuring said container at least at three different planar elevations during each profile scan of the said container.

18. Combined apparatus for inspecting the shape of a generally cylindrical or oval article which comprises a series of at least three lamps located at three different angles along one side of said article, a series of at least three similar photosensors located in juxtaposition at three different complemental angles along the other side of said article, each of said photosensors adapted to scan the back-lighted profile of said article in intermediate relation during operation of the respective juxtaposed lamps, electronic means for obtaining at least one external measurement from each of the three profiles at the same elevation to permit calculation of the major and minor axes of said article independently of orientation, and means for rejecting the said article as defective when the deviation of the major and minor axes exceeds established maximum or minimum dimensions.

19. Combined apparatus in accordance with claim 18, including a lens system positioned intermediate said lamps and said article to illuminate said article in back-lighted profile with essentially collimated light.

20. Combined apparatus in accordance with claim 18, including an anamorphic lens system intermediate said article and said series of three similar photosensors to increase the width-to-height viewing ratio of said article.

21. Combined apparatus in accordance with claim 18, wherein the said series of three lamps and said series of three similar photosensors are positioned at 45°, 90° and 135° with respect to said article, each pair of lamp and photosensor being juxtaposed from each other with said article disposed therebetween in line-of-sight location.

22. Combined apparatus in accordance with claim 18, wherein said electronic means is adapted to measure said article at least at three different planar elevations during each profile scan of the said article.

23. Combined apparatus for inspecting the shape of a generally cylindrical or oval container which comprises conveyor means for transporting the said container in upright relation in a lineal direction, a series of three stroboscopic lamps located at three different angles in an arcuate pattern facing a central region along one side of said conveyor means, an electrical power source adapted to illuminate said lamps briefly when said container is closely adjacent the central region, a series of three similar photosensors located in juxtaposition at three different complemental angles in an arcuate pattern along the other side of said container, each of said photosensors adapted to scan the profile of said container during operation of the respective juxtaposed stroboscopic lamps, electronic means for obtaining at least one measurement from each of the three profiles at the same elevation to permit calculation of the major and minor axes of said container independently of orientation, and means for rejecting the said container as defective when the deviation of the major and minor axes of said container exceeds established maximum or minimum dimensions.

* * * * *